United States Patent [19]

Cook

[11] 4,071,680

[45] Jan. 31, 1978

[54] 5'-DEOXY-5-FLUOROPYRIMIDINE NUCLEOSIDES

[75] Inventor: Alan Frederick Cook, Cedar Grove, N.J.

[73] Assignee: Hoffmann-La Roche Inc., Nutley, N.J.

[21] Appl. No.: 752,510

[22] Filed: Dec. 20, 1976

[51] Int. Cl.$^2$ ............................................. C07H 19/06
[52] U.S. Cl. ..................................... 536/23; 424/180; 536/22
[58] Field of Search .................................... 536/23, 22

[56] References Cited

U.S. PATENT DOCUMENTS

| 3,687,931 | 8/1972 | Verheyden et al. | 536/23 |
| 3,910,885 | 10/1975 | Moffatt et al. | 536/23 |
| 3,928,319 | 12/1975 | Jenkins et al. | 536/23 |

Primary Examiner—Johnnie R. Brown
Attorney, Agent, or Firm—Samuel L. Welt; Jon S. Saxe; George M. Gould

[57] ABSTRACT

Novel 5'-deoxy-5-fluoropyrimidine nucleosides are potent anti-tumor agents. Preferred compounds are 5'-deoxy-5-fluorocytidine and 5'-deoxy-5-fluorouridine.

4 Claims, No Drawings

5'-DEOXY-5-FLUOROPYRIMIDINE NUCLEOSIDES

BACKGROUND OF THE INVENTION

The introduction of a 5'-deoxy substituent into pyrimidine nucleosides has been previously described. Thus Wempen et al., *J. Amer. Chem. Soc.* 82, 1624 (1960) reported the synthesis of 5'-deoxy-uridine, 5'-deoxy-5'-fluoro-cytidine, and 5'-deoxy-5'-fluorouridine. Japanese Pat. No. 49-116081 describes the preparation of 5'-deoxy-cytidine by reduction of corresponding 5'-halo (Br or I) or 5'-methyl or benzylmercaptans. No antitumor activity was ascribed to either of the aforementioned final product compounds.

Falco and Fox, *J. Med. Chem.* 11, 148 (1968) describe the synthesis of 1-(5'-deoxy- $\beta$-D-arabinofuranosyl) cytosine. This compound was found to be inactive against L1210, leukemia and Burkitt's cell cultures presumably because such compound could not form a 5'-phosphorylated derivative.

Hein et al., *Nucleic Acids Research* 3, 1125 (1976) also have prepared 5'-deoxyuridine and 2',5'-dideoxyuridine by alternate reductive procedures. No biological activity is ascribed to the products produced.

Japanese Pat. No. 51-086481 discloses the preparation of 2',5'-dideoxy-5-fluorouridine from the corresponding 2',5'-dideoxy-5'-iodo compound. The product is indicated to be an anti-cancer agent inhibiting the growth of Yoshida sarcoma.

U.S. Pat. No. 3,687,931 teaches the preparation of 5'-deoxy-5'-chloro or bromo nucleosides using triphenylphosphine using carbon tetrachloride or carbon tetrabromide. The compounds are disclosed to have antibiotic, antimetabolic and enzyme inhibition activity.

Description of the Invention

The present invention relates to novel 5'-deoxy-5-fluoropyrimidine nucleosides useful as potent antitumor agents. In particular, the present invention relates to 5'-deoxy5-fluorocytidine, 5'-deoxy-5-fluoro-uridine and the acid addition salts thereof.

Compounds of the present invention are readily prepared starting from 5-fluorocytidine or 5-fluorouridine respectively by procedures analogous to those known in the art for the conversion of cytidine or uridine to the the corresponding 5'-deoxy compound. Thus, for example, the starting nucleoside can be halogenated in the 5'position either directly or more preferably after ketalization of the 2',3'-dioxy moieties using a conventional protecting group such as anisylidene, cyclohexylidene, methoxy methylidene or most preferably the isopropylidene or benzylidene groups. The resulting 5'-halo compound is then reduced either with a chemical reducing agent or utilizing catalytic hydrogenation. Finally, if protective groups have been employed, such groups are removed by hydrolysis in a manner known per se so as to yield the desired 5'-deoxy end products.

The conversion of 5-fluorocytidine or 5-fluorouridine to the 2',3'-ketal protected form can be carried out utilizing procedures known per se. Thus in one preferred embodiment the fluoronucleoside is treated with an organic sulfonic acid such as p-toluenesulfonic acid and a ketalizing agent such as 2,2-dimethoxypropane in a suitable organic solvent such as a ketonic solvent, i.e., acetone. The reaction is carried out at a temperature in the range of from about 0° to 60° C., most preferably at room temperature.

Introduction of the 5'-halo substituent can be carried out on either the starting 5-fluoronucleosides or, more preferably, on the 2',3'-diprotected compounds prepared as above. Preferred halogens for the purposes of the present invention are iodo and bromo. Thus, for example, the iodo group can be introduced by reaction of the desired substrate compound with a chemical iodinating agent. A suitable chemical iodinating agent is triphenylphosphite methiodide which can be employed with a polar non-protic organic solvent such as dimethylformamide at a temperature in the range of from 0° to 100° C., most preferably at room temperature. Introduction of a 5'-bromo group can be accomplished by use of a chemical brominating agent on the aforesaid substrates. Examples of chemical brominating agents include triphenylphosine plus carbon tetrabromide. Bromination can be carried out in a dipolar aprotic solvent such as dimethylformamide at a temperature in the range of from 10° to 100° C.

Conversion of the 5'-halo intermediates prepared as indicated above to the corresponding 5'-deoxy compounds can readily be accomplished by catalytic hydrogenation using a noble metal catalyst which may be supported such as palladium on carbon, palladium on barium sulphate, palladium, nickel, etc. in a protic polar solvent such as an alcohol preferably methanol. The reaction is conducted at a temperature in the range of from 0 to 60° C., preferably at room temperature and at a pressure of from 1 to 5 atm., most preferably at atmospheric pressure. The reaction is carried out in the presence of an organic base, preferably a tri-lower alkylamine such as triethylamine.

Chemical reducing agents can also be used to convert the 5'-halo compounds to the corresponding 5'-deoxy compounds. Suitable chemical agents include tributyl tin hydride, sodium cyanoborohydride or lithium triethylborohydride. A temperature in the range of from 0° to 100° C., can be employed. Suitable solvents for each of said agents are well known in the art.

Removal of the ketal protecting groups, if present, can be readily accomplished using procedures well known in the art. Thus, for example, the isopropylidene group is cleaved utilizing trifluoroacetic acid treatment at room temperature.

A further aspect of the present invention includes the novel intermediates produced in accordance with the aforesaid processes. Such novel intermediates include:
5'-deoxy-5'-iodo-2',3'-O-isopropylidene-5-fluorocytidine
5'-deoxy-2',3'-O-isopropylidene-5-fluorocytidine
5'-deoxy-5'-iodo-2',3'-O-isopropylidene-5-fluorouridine
5'-deoxy-2',3'-O-isopropylidene-5-fluorouridine
5'-deoxy-5'-iodo-5-fluorocytidine
5'-deoxy-5'-iodo-5-fluorouridine The final 5'-deoxy-5-fluoropyrimidine products of the present invention and their pharmaceutically acceptable acid addition salts are useful as anti-tumor agents. Thus, the instant compounds exhibit activity against Ehrlich carcinoma and sarcoma 180 in mice over a very wide range of dosages both orally and parenterally.

As used herein the term "pharmaceutically acceptable salts" is meant to include non-toxic salts such as formed from acids selected from the group consisting of inorganic mineral acids such as the hydrochloride, hydrobromide, phosphate, sulphate or nitrate; or from organic acids, for example, acetate, formate, maleate, fumerate, benzoate and the like.

EXAMPLE 1

2,3'-O-Isopropylidene-5-Fluorocytidine

A suspension of 5-fluorocytidine (92g, 353 mmol) and p-toluene-sulfonic acid monohydrate (80g) in acetone (1500 ml) and 2,2-dimethoxypropane (200 ml) was stirred at room temperature for 2 hr. Excess solid sodium bicarbonate was added and the mixture stirred until the acid had been completely neutralized. The solids were filtered off and washed with acetone and the filtrate and washings were evaporated to dryness. The residue was triturated with hot ethyl acetate (700 ml) and crystallization slowly commenced. After storage overnight the solid was collected, washed with ethyl acetate, and dried in vacuo. Yield = 99.5g (331 mmol, 94%). A sample was recrystallized from methanol-/ethyl acetate, mp. 182°–184°. UV(CH$_3$OH)λ max 240 mμ(ε 9420)λ max 282 mμ (ε 7280). NMR (Me$_2$SO-d$_6$) δ 1.28, 1.47 (s, 3, (CH$_3$)$_2$C).

Found: C 47.73, N 5.42, N 13.88, F 6.03. C$_{12}$H$_{16}$FN$_3$O$_5$ Calcd: C 47.84, H 5.35, N 13.95, F 6.31.

EXAMPLE 2

5'-Deoxy-5'-Iodo-2',3'-O-Isopropylidene-5-Fluorocytidine

A solution of 2',3'-O-isopropylidene-5-fluorocytidine (32g, 106 mmol) and triphenylphosphite methiodide (60g, 133 mmol) in DMF (300 ml, dry) was stored at room temperature for 1.5 hr. Methanol (100ml) was added, and after 30 min. the solution was evaporated to an oil and partitioned between ethyl acetate (700 ml) and aqueous sodium thiosulfate (5%, 700 ml). The ethyl acetate layer was washed once with aqueous thiosulfate (700 ml) and twice with water (700 ml), and evaporated to an oil. This material was dissolved in hot ethyl acetate (400 ml) and hexane was added to the hot solution until crystallization commenced. After storage at 0° the crystals were collected, washed with hexane, and dried in vacuo. A second batch of crystals was obtained from the liquors. Total yield = 30.1g (73.1 mmol, 69%). mp 192–194°. UV (CH$_3$OH) λ max 245 mμ (ε 9500) λ max 280 mμ (ε 6620). NMR (Me$_2$SO-d$_6$) δ 8.00 (d, 1, J = 7 Hz, CHCF) δ 1.28, 1.47 Hz(s, 3, (CH$_3$)$_2$C) δ 3.45 (m, 2, CH$_2$I).

Found: C 35.29, H 3.85, N 10.11, I 30.77. C$_{12}$H$_{15}$FIN$_3$O$_4$ Calcd: C 35.05, H 3.68, N 10.22, I 30.86.

EXAMPLE 3

5'-Deoxy-2',3'-O-isopropylidene-5-fluorocytidine

A solution of 5'-deoxy-5'-iodo-2',3'-O-isopropylidene-5-fluorocytidine (48g, 116.5 mmol) in methanol (500 ml) and triethylamine (20ml) was treated with hydrogen at atmospheric pressure in the presence of palladium on carbon (5%, 25g) for 30 min. at room temperature. During this time the suspension was agitated using a "VIBROMIX" vibrator. The catalyst removed by filtration through celite, and the filtrate was evaporated to dryness and triturated with ethyl acetate (200 ml). After storage overnight the crystals were removed by filtration, and the filtrate was evaporated to approximately 100 ml and again stored overnight. A second batch of crystals was removed by filtration, and the filtrate was evaporated to dryness, pumped in vacuo, to give 5'-deoxy-2',3'-O-isopropylidene-5-fluorocytidine as a foam 31g (93%). This material was characterized by formation of a crystalline picrate salt, mp 168°–170°. uv (CH$_3$OH) λ max 237–238 mμ(ε 20,700), λmax 282 mμ(ε 9,400), λ max 353–354mμ(ε 15,300). NMR ((CH$_3$)$_2$SO-d$_6$) δ 8.58 (S, 2, picrate) δ 8.29 (d, 1, J = 7 Hz, CHCF) δ5.72 (d,J= 4 Hz, C'$_1$) δ1.47, 1.28 (S, 3, (CH$_3$)$_2$C) δ 1.31 (d, 3, J = 6 Hz, C$\underline{H}$$_3$CH).

EXAMPLE 4

5'-Deoxy-5-Fluorocytidine

5'-Deoxy-2',3'-O-isopropylidene-5-fluorocytidine (31 g) was treated with 90% trifluoroacetic acid (200 ml) for 40 minutes. The solution was evaporated to dryness, repeatedly evaporated with portions of ethanol to remove residual water and trifluoroacetic acid, and dissolved in ethyl acetate (400 ml). Triethylamine was added to alkalinity, and after a few minutes crystallization commenced. After storage overnight the crystals were collected, washed with ethyl acetate and dried in vacuo. Yield = 14g (49%). Additional material was obtained by chromatography of the mother liquors on a silica gel column (600 g) which was eluted with ethyl acetate (4 liters) followed by ethyl acetate/methanol) (5:1, 4 liters). The appropriate fractions were evaporated to dryness and applied to a Dowex 50 column(H$^+$)2.3 × 60 cm. After a preliminary water wash, the required material was recovered by elution with aqueous ammonia (N). The ammonia fractions were evaporated to dryness and the residue recrystallized from ethanol. In this way an additional 6.7g of 5'-deoxy-5-fluorocytidine was obtained. Total yield = 20.7 g (78%). mp 209°–211° dec. UV(H$_2$O)λ max 238 mμ (ε 7900)λ max 281 mμ (ε 7860) sh 210 mμ (ε 9580). NMR (Me)$_2$SO-d$_6$) δ 7.62 (d,1,J = 7 Hz, CHCF) δ 1.31 (d, 3, J = 6 Hz, C$\underline{H}$$_3$-CH).

Found: C 44.08, H 4.93, N 17.14, F 7.75 C$_9$H$_{12}$FN$_3$O$_4$ Calcd: C 44.09, H 5.09, N 17.25, F 7.83.

EXAMPLE 5

2',3'-O-Isopropylidene-5-Fluorouridine

A suspension of 5-fluorouridine (50g, 191 mmol) and p-toluenesulfonic acid monohydrate (39.3g) in acetone (750 ml) and 2,2-dimethoxypropane (94 ml) was stirred at room temperature for 50 min. Excess solid sodium bicarbonate was added to the clear solution, and the mixture was stirred until neutral. The solids were removed by filtration and washed with acetone, and the filtrate and washings were combined and evaporated to dryness. The residual solid was recrystallized from ethyl acetate (2 liters), yield 48g (83%). mp 196°–197°. UV(C$_2$H$_5$OH) λ max 207mμ (ε 9300) λ max 268 mμ (ε8880). NMR ((CH$_3$)$_2$SO-d$_6$) δ 8.12 (d, 1, J = 7 Hz, CHCF) δ 1.25, 1.49 (s, 3, (CH$_3$)$_2$C).

Found: C 47.93, H 5.27, N 9.44, F 6.23. C$_{12}$H$_{15}$FN$_2$O$_6$ Calcd: C 47.68, H 5.00, N 9.27, F. 6.29.

EXAMPLE 6

5'-Deoxy-5'-Iodo-2',3'-O-Isopropylidene-5-Fluorouridine

A solution of 2',3'-O-isopropylidene-5-fluorouridine (46.4g, 153.5 mmol) in DMF (250 ml, dry) was treated with triphenylphosphite methiodide (86.7g) and stored at room temperature for 50 min. Methanol (250 ml) was added and after 30 min. the solution was evaporated to an oil and partitioned between ethyl acetate (1 liter) and aqueous sodium thiosulfate (5%, 1 liter). The ethyl acetate layer was washed with water (2 × 1 liter), dried overnight over sodium sulfate, and evaporated to dryness. The oil was crystallized from ethyl acetate (350 ml). Yield = 52.9g (85%). mp 202°–203.5°. UV(CH$_3$OH) λ max 264 mμ (ε 9300). NMR ((CH$_3$)$_2$SO-d$_6$) δ 8.10 (d, 1, J = 6 Hz, CHCF) δ 3.43 (m, 2, CH$_2$I) δ 1.30, 1.49 (s, 3, (CH$_3$)$_2$C).

Found: C 35.02, H 3.36, N 6.57. C$_{12}$H$_{14}$FIN$_2$O$_5$ Calcd: C 34.97, H 3.42, N 6.80.

EXAMPLE 7

5′-Deoxy-5-Fluorouridine

A solution of 5′-deoxy′5′-iodo-2′,3′-O-isopropylidene-5-flourouridine (24g) in methanol (800 ml) and triethylamine (15ml) was treated with hydrogen at atmospheric pressure in the presence of palladium on carbon (12g, 5%) for 90 min. at room temperature. The reaction was agitated during this time using a "Vibromix" vibrator. The catalyst was removed by filtration through celite and washed with methanol, and the combined filtrate and washings were evaporated to dryness and triturated with ethyl acetate (200 ml) for 1 hr. and the crystals were removed by filtration. The filtrate was evaporated to approximately half volume, stored overnight and filtered again to remove a second batch of crystals. The filtrate was evaporated to dryness, pumped in vacuo and the resulting 5′-deoxy-2′,3′-O-isopropylidene-5-fluorouridine treated with aqueous trifluoroacetic acid (90%, 200ml) for 1 hr. The product was evaporated to dryness, repeatedly coevaporated with ethanol to remove water and trifluoroacetic acid, and recrystallized from ethyl acetate to give 5′-deoxy-5-fluorouridine 11.35g (79%). mp 189°–190°. UV(CH$_3$OH) λ max 268-269 mμ (δ 8550). NMR ((CH$_3$)$_2$SO-d$_6$) δ 7.87 (d, 1, J = 7 Hz, CHCF) δ1.28 (d, 3, J = 6 Hz, C$\underline{H}$$_3$CH).

Found: C 44.01, H 4.43, N 11.28, F 7.55. C$_9$H$_{11}$FN$_2$O$_5$ Calcd: C 43.90, H 4.50, N 11.38, F 7.72.

EXAMPLE 8

5′-Deoxy-5′-iodo-5-Fluorouridine a. From 5-Fluorouridine

A solution of 5-fluorouridine (2.62 g, 10 mmol) in DMF (50 ml) was treated with triphenylphosphite methiodide (5.42 g, 12 mmol) for 1.75 hr at room temperature, Methanol (10 ml) was added and after 30 minutes the solution was evaporated to an oil, dissolved in ethyl acetate (30 ml) and applied to a silica gel column (500 g, Merck). The column was eluted with ethyl acetate and 20 ml fractions were collected. Fractions 61–130 were combined, evaporated to dryness and dissolved in hot ethyl acetate (50 ml). Addition of hexane (10 ml) gave crystalline material. After storage at room temperature overnight, the crystals were collected, washed with hexane and dried in vacuo. A second crop was obtained from the mother liquors. Total yield = 1.13 g (30%). mp 174.5°–175.5°, uv (CH$_3$OH) λ max 267-268mμ(ε 9,130) nmr (MeSO-d$_6$) δ 8.0 (d, 1, J = 7 Hz, CHCF) δ 11.92 (S, 1, NH) δ 3.5 (m, 2, CH$_2$I).

Found: C, 29.26; H, 2.73; N, 7.72; I, 33.89. C$_9$H$_{10}$FIN$_2$O$_5$ calcd: C, 29.05; H, 2.71; N, 7.53; I, 34.11.

b. From 5′-Deoxy-5′-iodo-2′,3′-O-Isopropylidene-5-Fluorouridine

5′-Deoxy-5′-iodo-2′,3′-O-isopropylidene-5-fluorouridine (4 g) was treated with trifluoroacetic acid/water (9:1, 30 ml) for 15 minutes at room temperature. The solution was evaporated to dryness, co-evaporated with ethanol (2 × 100 ml) and the residue was recrystallized from ethyl acetate. Yield = 1.865 g (88%).

EXAMPLE 9

5′-Deoxy-5-Fluorouridine-from 5′-Deoxy-5′-iodo-5-fluorouridine

A solution of 5′-deoxy-5′-iodo-5-fluorouridine (291 mg, 0.75 mmol) in methanol (10 ml) and triethylamine (0.5 ml) was hydrogenated using hydrogen at atmospheric pressure in the presence of palladium on carbon (5%, 145 mg). After 1.5 hours the catalyst was removed by filtration and the filtrate was evaporated to dryness and dissolved in a minimum amount of hot ethyl acetate. On cooling, crystals of triethylammonium iodide were deposited. These were removed by filtration and the filtrate was evaporated to dryness and recrystallized from ethanol. Yield of 5′-deoxy-5-fluorouridine = 130 mg (68%).

EXAMPLE 10

5′-Deoxy-5′-Iodo-5-Fluorocytidine a. From 5-fluorocytidine

A solution of 5-fluorocytidine (2.61 g, 10 mmol) in DMF (50 ml) was treated with triphenylphosphite methiodide (5.42 g, 12 mmol) for 5 hours at room temperature. Since thin layer chromatography of the reaction mixture indicated the presence of starting material, a further portion of triphenylphosphite methiodide (5.42 g) was added and the reaction allowed to proceed for an additional 90 minutes. Methanol (10 ml) was added and after 15 minutes, the solution was evaporated to an oil, dissolved in ethyl acetate/methanol (1:1, 30 ml) and applied to a silica gel column (600 g). The column was eluted with ethyl acetate/methanol (10:1) and 20 ml fractions were collected. Fractions 190–280 were combined, evaporated to a yellow solid and dissolved in water (30 ml). The solution was applied to a Dowex 50 (H$^+$) column (2.3 × 40 cm) and after a preliminary water wash, the column was eluted with 2N ammonium hydroxide. The eluate was evaporated to a crystalline mass, 200 mg (5.4%). Recrystallization from ethanol gave pure material. mp 187°–189°, uv(CH$_3$OH) λ max 242–243 mμ(ε8950), λ max 280–281 mμ(ε7400) nmr (Me$_2$SO-d$_6$) δ7.86 (d, 1, J = 7Hz, CHCF) δ7.68 (S, 2, NH$_2$) δ5.82(q, 1, J = 5.5 Hz, 2 Hz, C′$_1$-H) δ5.35, 5.24 (d, 1, J = 6 Hz, OH).

Found: C, 29.32; H, 2.99; N, 11.32. C$_9$H$_{11}$FIN$_3$O$_4$ calcd: C, 29.13; H, 2.99; N, 11.32.

b. From 5′-Deoxy-5′-iodo-2′,3′-O-Isopropylidene-5-Fluorocytidine

A solution of 5′-deoxy-5′-iodo-2′,3′-O-isopropylidene-5-fluorocytidine (20 g) in trifluoroacetic acid/water (9:1, 100 ml) was stored at room temperature for 70 min. The solution was evaporated to dryness, co-evaporated with ethanol (2 × 200 ml) and dissolved in ethyl acetate (200 ml). Triethylamine was added to neutrality, and after storage overnight the crystals were collected and dried. Yield = 16.8 g (93%).

EXAMPLE 11

Antitumor testing

All compounds were dissolved in water for administration to animals.

Sarcoma 180

Small pieces of tumor (20–30mg) were implanted subcutaneously by trocar into the right inguinal region of 18–20 g albino mice. The fragments were obtained from donors bearing firm subcutaneous tumors implanted 7–10 days previously. Treatment was begun on the day of implantation and continued once daily for a total of 8 treatments. The animals were sacrificed 8 days after implantation and the tumors excised and weighed. The ratio of the average weight of the tumors from the untreated control group (C) divided by the average weight of the tumors from the treated group (T) was calculated. The percent inhibition of tumor growth was calculated from the formula:

% Inhibition = 100 (C-T)/C . The compound was considered to be active at a particular dose if % inhibition ≧ 50%.

Ehrlich Carcinoma

The solid form of this tumor was produced by subcutaneous implantation of 0.5 ml of a 1–10 saline - diluted ascitic tumor cell suspensions derived from 18–20 g albino donor mice implanted 7–10 days previously. Treatment and evaluation procedures were identical to those used for Sarcoma 180.

Results obtained from experiments, utilizing compounds of the present invention and representative prior art compounds are summarized below in Table 1.

Table 1

| Effect of Pyrimidine Nucleosides Against Sarcoma 180 Tumor in Mice (active doses are those which produce ≧50% tumor inhibition) | | | |
|---|---|---|---|
| Compound | Dose mg/kg × 8 | No. of Survivors/ No. Tested | Percent Inhibition of tumor growth |
| 5'-Deoxy-5-Fluorocytidine | 400 ip | 14/16 | 95 |
|  | 200 ip | 14/16 | 93 |
|  | 100 ip | 16/16 | 86 |
|  | 50 ip | 15/16 | 72 |
|  | 25 ip | 16/16 | 64 |
|  | 12.5 ip | 8/8 | 37 |
| " | 400 po | 15/16 | 92 |
|  | 200 po | 13/16 | 82 |
|  | 100 po | 14/16 | 76 |
|  | 50 po | 16/16 | 65 |
|  | 25 po | 15/16 | 76 |
|  | 12.5 po | 23/24 | 62 |
|  | 6.25 po | 7/8 | 26 |
| 5'-Deoxy-5-Fluorouridine | 200 ip | 15/16 | 88 |
|  | 100 ip | 16/16 | 88 |
|  | 50 ip | 15/16 | 89 |
|  | 25 ip | 14/16 | 67 |
|  | 12.5 ip | 7/8 | 43 |
| " | 400 lpo | 15/16 | 90 |
|  | 200 po | 15/16 | 90 |
|  | 100 po | 16/16 | 83 |
|  | 50 po | 16/16 | 80 |
|  | 25 po | 16/16 | 75 |
|  | 12.5 po | 16/16 | 73 |
|  | 6.25 po | 15/15 | 68 |
|  | 3.12 po | 16/16 | 51 |
|  | 1.56 po | 8/8 | 30 |
| 2',5'-Dideoxy-5-Fluorouridine (5'-Deoxy-FUDR) | 400 ip | 14/16 | 81 |
|  | 200 ip | 14/16 | 68 |
|  | 100 ip | 16/16 | 37 |
|  | 200 po | 8/8 | 34 |
| 5'-Deoxyuridine | 200 ip | 8/8 | 9 |
|  | 100 ip | 8/8 | 41 |

| Effect of pyrimidine Nucleosides Against Ehrlich Carcinoma in Mice | | | |
|---|---|---|---|
| Compound | Dose mg/kg × 8 | No. Survivors/ No. Tested | Percent Inhibition of Tumor Growth |
| 5'-Deoxy-5-fluorocytidine | 400 ip | 14/15 | 91 |
|  | 200 ip | 23/24 | 72 |
|  | 100 ip | 16/16 | 65 |
|  | 50 ip | 23/24 | 57 |
|  | 25 ip | 15/15 | 45 |
| " | 800 po | 8/8 | 99 |
|  | 400 po | 16/16 | 95 |
|  | 200 po | 24/24 | 80 |
|  | 100 po | 24/24 | 71 |
|  | 50 po | 16/16 | 58 |
|  | 25 po | 16/16 | 37 |
| 5'-Deoxy-5-fluorouridine | 400 ip | 14/16 | 98 |
|  | 200 ip | 22/24 | 86 |
|  | 100 ip | 20/24 | 71 |
|  | 50 ip | 23/24 | 59 |
|  | 25 ip | 22/24 | 43 |
| " | 800 po | 8/8 | 99 |
|  | 400 po | 16/16 | 98 |
|  | 200 po | 16/16 | 90 |
|  | 100 po | 15/15 | 70 |
|  | 50 po | 8/8 | 56 |
|  | 25 po | 8/8 | 27 |

Example 12
WET GRANULATION TABLET FORMULATION

|  |  | mg/tab | mg/tab |
|---|---|---|---|
| 1. | 5'-deoxy-5-fluorouridine | 250 | 500 |
| 2. | Pregelatinized Starch | 25 | 50 |
| 3. | Modified Starch | 25 | 50 |
| 4. | Corn Starch | 25 | 50 |
| 5. | Stearic Acid | 2.5 | 2.5 |
| 6. | Magnesium Stearate | 1.5 | 3.0 |
|  |  | 329.0 | 655.5 |

-continued

Example 12
WET GRANULATION TABLET FORMULATION

| | mg/tab | mg/tab |
|---|---|---|

Procedure
1. Mix item 1, 2, 3 and 4. Granulate with water, dry overnight and mill.
2. Add item 5 and 6 as a premix. Mix for 5 minutes. Compress at suitable pressure.

Example 13
CAPSULE FORMULATIONS

| | | mg/tab | mg/tab |
|---|---|---|---|
| 1. | 5'-deoxy-5-fluorouridine | 250 | 500 |
| 2. | Corn Starch | 50 | 50 |
| 3. | Magnesium Stearate | 2 | 5 |
| 4. | Talc | 10 | 20 |
| | | 312 mg | 575 mg |

Procedure
1. Mix Item 1 and 2 in a suitable mixer for 10 min.
2. Add Item 3 and 4 to the mixture in Step 1 and mix for 5 minutes.
3. Fill on suitable machine.

Example 14
WET GRANULATION TABLET FORMULATION

| | | mg/tab | mg/tab |
|---|---|---|---|
| 1. | 5'-deoxy-5-fluorouridine | 250 | 500 |
| 2. | Polyvinyl Pyrrolidone | 25 | 50 |
| 3. | Modified Starch | 25 | 50 |
| 4. | Corn Starch | 25 | 50 |
| 5. | Magnesium Stearate | 2.5 | 5.0 |
| | | 327.5 | 655.0 |

Procedure
1. Mix Item 1, 3 and 4 in a suitable mixer. Granulate with Item 2 in alcohol. Dry overnight and mill.
2. Add Item 5 and 6 in the granulation in Step 1 and compress on a suitable press.

Example 15
CAPSULE FORMULATIONS

| | | mg/tab | mg/tab |
|---|---|---|---|
| 1. | 5'-deoxy-5-fluorocytidine | 250 | 500 |
| 2. | Corn Starch | 50 | 50 |
| 3. | Magnesium Stearate | 2 | 5 |
| 4. | Talc | 10 | 20 |
| | | 312 mg | 575 mg |

Procedure
1. Mix Item 1 and 2 in a suitable mixer for 10 min.
2. Add Item 3 and 4 to the mixture in Step 1 and mix for 5 minutes.
3. Fill on suitable machine.

Example 16
WET GRANULATION TABLET FORMULATION

| | | mg/tab | mg/tab |
|---|---|---|---|
| 1. | 5'-deoxy-5-fluorocytidine | 250 | 500 |
| 2. | Pregelatinized Starch | 25 | 50 |
| 3. | Modified Starch | 25 | 50 |
| 4. | Corn Starch | 25 | 50 |
| 5. | Stearic Acid | 2.5 | 2.5 |
| 6. | Magnesium Stearate | 1.5 | 3.0 |
| | | 329.0 | 653.5 |

Procedure
1. Mix item 1, 2, 3 and 4. Granulate with water, dry, mill.
2. Add item 5 and 6 as a premix. Mix for 5 minutes. Compress at suitable press.

Example 17
WET GRANULATION TABLET FORMULATION

| | | mg/tab | mg/tab |
|---|---|---|---|
| 1. | 5'-deoxy-5-fluorocytidine | 250 | 500 |
| 2. | Polyvinyl Pyrrolidone | 25 | 50 |
| 3. | Modified Starch | 25 | 50 |
| 4. | Corn Starch | 25 | 50 |
| 5. | Magnesium Stearate | 2.5 | 5.0 |
| | | 327.5 | 655.0 |

Procedure
1. Mix Item 1, 3 and 4 in a suitable mixer. Granulate with Item 2 in alcohol. Dry overnight and mill.
2. Add Item 5 and 6 in the granulation in Step 1 and compress on a suitable press.

EXAMPLE 18

Dry-Parenteral Dosage Forms

1. A total of five grams of either 5'-deoxy-5-fluorocytidine or 5'-deoxy-5-fluorouridine is dissolved in 75 ml. of distilled water, the solution is subjected to a bacteriological filtration, and then divided aseptically into 10 sterile vials. The solution is then freeze dried to yield 500 mg of sterile dry solid per vial.

2. Clean, lint-free crystals of either 5'-deoxy-5-fluorocytidine or 5'-deoxy5-fluorouridine in the amount of 500 mg per vial or ampoule are sealed in the receptacle and are heat sterilized.

The aforesaid dry dosage forms are reconstituted before use by adding a suitable sterile aqueous solvent such as water for injection or isotonic sodium chloride or 5% dextrose for parenteral administration.

I claim:
1. A 5'-deoxy-5-fluoropyrimidine nucleoside selected from the group consisting of 5'-deoxy-5-fluorocytidine, 5'-deoxy-5-fluorouridine and the pharmaceutically acceptable acid addition salts thereof.
2. The compound of claim 1 which is 5'-deoxy-5-fluorocytidine.
3. The compound of claim 1 which is 5'-deoxy-5-fluorouridine.
4. A 5'-deoxy-2',3'-O-isopropylidene-5-fluoropyrimidine-nucleoside selected from 5'-deoxy-2',3'-isopropylidene-5-fluorocytidine and 5'-deoxy-2',3'-O-isopropylidene5-fluorouridine.

* * * * *